(12) United States Patent
Bonner et al.

(10) Patent No.: US 12,377,278 B2
(45) Date of Patent: Aug. 5, 2025

(54) POLYMERIC ENCLOSURE FOR IMPLANTABLE MEDICAL DEVICE

(71) Applicant: Medtronic, Inc., Minneapolis, MN (US)

(72) Inventors: Matthew D. Bonner, Plymouth, MN (US); Pradipta K. Das, Plymouth, MN (US); Allan E. Dienes, Ramsey, MN (US); Jeffrey Sandstrom, Scandia, MN (US); Jeffrey S. Voss, White Bear Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 646 days.

(21) Appl. No.: 17/649,593

(22) Filed: Feb. 1, 2022

(65) Prior Publication Data

US 2022/0273956 A1  Sep. 1, 2022

Related U.S. Application Data

(60) Provisional application No. 63/154,049, filed on Feb. 26, 2021.

(51) Int. Cl.
*A61N 1/375* (2006.01)
*B29C 45/14* (2006.01)
(Continued)

(52) U.S. Cl.
CPC ....... *A61N 1/3758* (2013.01); *A61N 1/37512* (2017.08); *A61N 1/3752* (2013.01);
(Continued)

(58) Field of Classification Search
CPC . A61N 1/3758; A61N 1/37512; A61N 1/3752
See application file for complete search history.

(56) References Cited

U.S. PATENT DOCUMENTS 3,057,356 A * 10/1962 Greatbatch ............ A61N 1/362
607/9
5,851,221 A 12/1998 Rieder et al.
(Continued)

FOREIGN PATENT DOCUMENTS

CN  2455271 Y  10/2001
EP  0732124 A2  9/1996

OTHER PUBLICATIONS

International Search Report and Written Opinion of International Application No. PCT/US2022/014822, dated May 3, 2022, 10 pp.
(Continued)

*Primary Examiner* — Eugene T Wu
(74) *Attorney, Agent, or Firm* — Shumaker & Sieffert, P.A.

(57) ABSTRACT

An implantable medical device system is configured to generate signals and deliver the signals to a heart of a patient. The implantable medical device system includes electronic circuitry configured to deliver cardiac pacing, couplings for an implantable medical lead receptacle, at least some of the couplings electrically connected with the electronic circuitry, a polymeric enclosure having the electronic circuitry contained therein, the polymeric enclosure formed of polymeric material filled around the electronic circuitry and couplings and forming the implantable medical lead receptacle. The implantable medical device may include a first cavity filled with a first material and a second cavity filled with a second material, and the first material is different than the second material.

5 Claims, 9 Drawing Sheets

(51) Int. Cl.
  *B29K 63/00* (2006.01)
  *B29K 105/00* (2006.01)
  *B29L 31/00* (2006.01)
  *B33Y 10/00* (2015.01)
  *B33Y 80/00* (2015.01)

(52) U.S. Cl.
  CPC .......... *B29C 45/14* (2013.01); *B29K 2063/00* (2013.01); *B29K 2105/0097* (2013.01); *B29L 2031/7534* (2013.01); *B33Y 10/00* (2014.12); *B33Y 80/00* (2014.12)

(56) References Cited

U.S. PATENT DOCUMENTS

| | | | |
|---|---|---|---|
| 5,899,930 A * | 5/1999 | Flynn | A61N 1/3752 607/37 |
| 6,428,368 B1 | 8/2002 | Hawkins et al. | |
| 6,491,639 B1 | 12/2002 | Turcott | |
| 6,757,566 B2 | 6/2004 | Weiner et al. | |
| 6,862,478 B1 | 3/2005 | Goldstein | |
| 6,903,268 B2 | 6/2005 | Marshall et al. | |
| 7,912,549 B2 | 3/2011 | Mueller et al. | |
| 8,290,592 B2 | 10/2012 | Kane et al. | |
| 8,355,785 B1 | 1/2013 | Hammond et al. | |
| 8,509,899 B2 | 8/2013 | Sommer et al. | |
| 9,032,614 B2 | 5/2015 | Specht | |
| 9,149,644 B2 | 10/2015 | Biggs, Jr. et al. | |
| 9,220,916 B2 | 12/2015 | Imran | |
| 9,393,407 B2 | 7/2016 | Bar-Cohen et al. | |
| 9,526,891 B2 | 12/2016 | Eggen et al. | |
| 9,962,552 B2 | 5/2018 | Seeley et al. | |
| 9,968,793 B2 | 5/2018 | Glynn et al. | |
| 10,112,045 B2 | 10/2018 | Anderson et al. | |
| 2008/0033500 A1 * | 2/2008 | Strother | A61N 1/375 607/36 |
| 2008/0234591 A1 | 9/2008 | Scinicariello et al. | |
| 2016/0166825 A1 | 6/2016 | Henschel et al. | |
| 2019/0083800 A1 | 3/2019 | Yang et al. | |
| 2020/0014152 A1 | 1/2020 | Henschel et al. | |

OTHER PUBLICATIONS

Model Pacemaker, Museum of Design in Plastics, retrieved from https://www.modip.ac.uk/artefact/aibdc-008433, on May 3, 2022, 5 pp.

* cited by examiner

POLYMERIC ENCLOSURE FOR IMPLANTABLE MEDICAL DEVICE

This application claims the benefit of U.S. Provisional Application Ser. No. 63/154,049, filed Feb. 26, 2021, the entire content of which is incorporated herein by reference.

TECHNICAL FIELD

The disclosure relates generally to medical device systems and, more particularly, methods of manufacturing cardiac therapy delivery devices.

BACKGROUND

Some types of implantable medical devices, such as cardiac pacemakers or implantable cardioverter defibrillators, provide electrical therapy to a heart of a patient via electrodes of one or more implantable leads. The electrical therapy may be delivered to the heart for pacing, cardioversion or defibrillation. The implantable medical device may include electronic circuitry to deliver the electrical therapy, where the electronic circuitry is encapsulated by a housing, such as a metal titanium housing.

SUMMARY

In general, this disclosure is directed to techniques for providing a polymeric enclosure for an implantable medical device. The polymeric enclosure provides mechanical strength, electrical isolation of the components therein, prevents moisture and fluid ingress into the implantable medical device system, and/or provides other benefits.

In one example, this disclosure describes a method for forming an implantable medical device with a polymeric enclosure, the method comprising: inserting electrical and mechanical couplings for an implantable medical lead receptacle into a first set of openings of a pre-formed polymeric structure, inserting a set of electronics within a second set of openings of the pre-formed polymeric structure, filling the first set of openings around the electrical and mechanical couplings with a first polymeric material, and filling the second set of openings around the set of electronics with a second polymeric material. In some examples, the first polymeric material is different than the second polymeric material.

In one example, this disclosure describes a method for forming an implantable medical device with a polymeric enclosure, the method comprising: inserting a set of electronics and couplings for an implantable lead receptacle into a set of openings of a fixture, electrically coupling the set of electronics and couplings creating a subassembly, disposing the subassembly within a mold; and disposing polymeric material around the set of electronics and couplings forming the polymeric enclosure for the implantable medical device with polymeric material.

In another example, this disclosure describes an implantable medical device system comprising: electronic circuitry configured to deliver cardiac pacing, couplings for an implantable medical lead receptacle, at least some of the couplings electrically connected with the electronic circuitry, and a polymeric enclosure having the electronic circuitry contained therein, the polymeric enclosure formed of polymeric material filled around the electronic circuitry and couplings and forming the implantable medical lead receptacle.

This summary is intended to provide an overview of the subject matter described in this disclosure. It is not intended to provide an exclusive or exhaustive explanation of the methods and systems described in detail within the accompanying drawings and description below. The details of one or more aspects of the disclosure are set forth in the accompanying drawings and the description below.

BRIEF DESCRIPTION OF DRAWINGS

The details of one or more examples of this disclosure are set forth in the accompanying drawings and the description below. Other features, objects, and advantages of this disclosure will be apparent from the description and drawings, and from the claims.

DETAILED DESCRIPTION

In general, this disclosure describes example techniques related to implantable medical devices having a polymeric enclosure and fabricating implantable medical devices with a polymeric enclosure. In some examples, the implantable medical device includes a polymeric enclosure rather than a metallic enclosure as is present in conventional implantable medical devices. The implantable medical device may be hermetically sealed and may include a lead connector and electronics in a single structure of polymeric material that provides mechanical strength and integrity, electrical isolation, and prevents moisture and fluid ingress. In some examples, the implantable medical device is a pacemaker, which may be configured for more temporary use than conventional pacemakers, e.g., for a number of months, rather than years.

Figure 1:
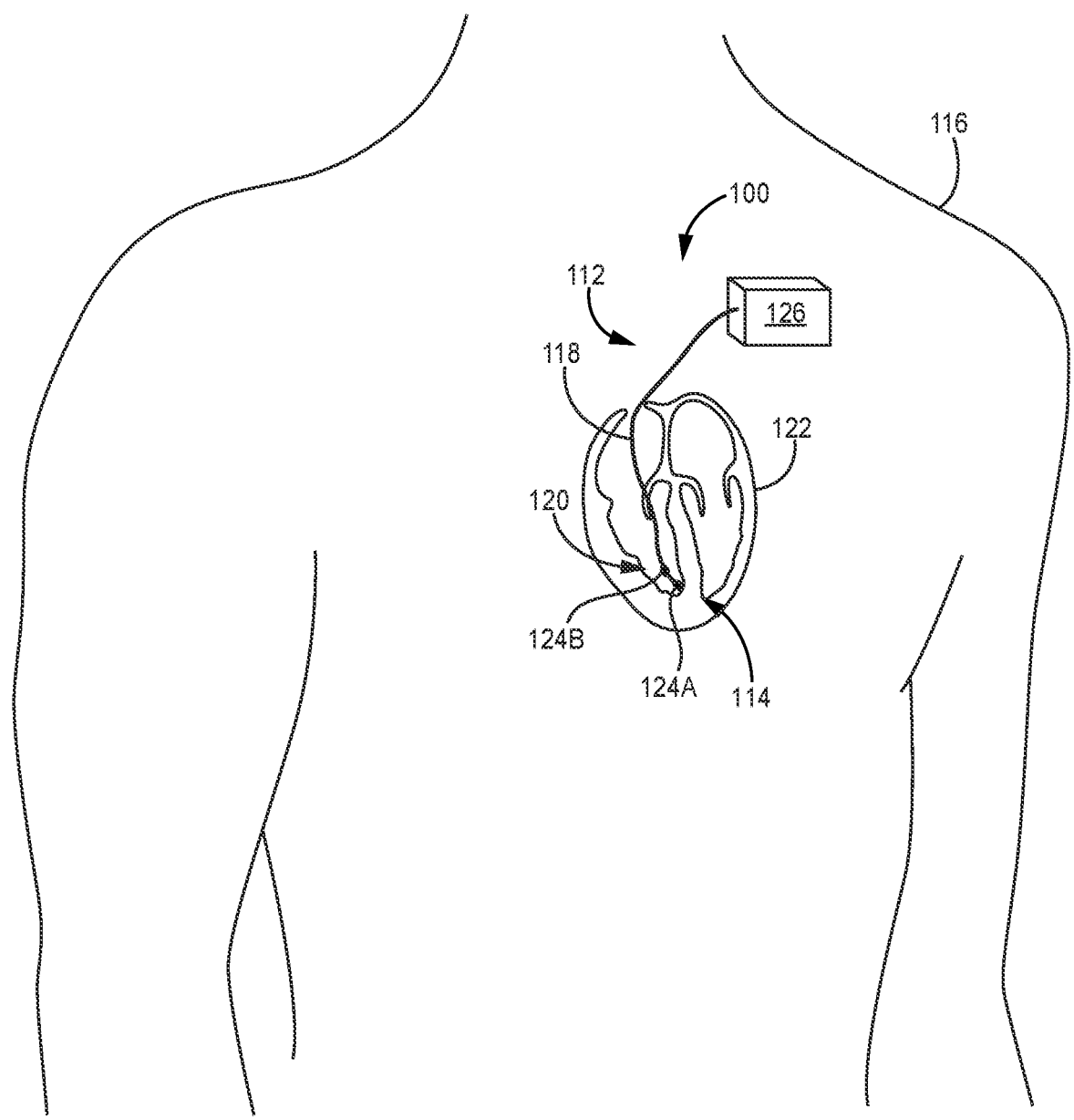
FIG. 1 is conceptual diagram illustrating an example implantable medical device system in accordance with one or more aspects of this disclosure.

FIG. 1 is a conceptual diagram illustrating a portion of an example implantable medical device system 100 in accordance with one or more aspects of this disclosure. Implantable medical device system 100 may function as a single chamber, e.g., ventricular, pacemaker, as illustrated by the example of FIG. 1, or as dual-chamber pacemaker that delivers pacing to a heart 122 of patient 116.

In the example of FIG. 1, implantable medical device system 100 includes one or more implantable medical leads 112 and an implantable medical device (IMD) 126. Implantable medical lead 112 includes an elongated lead body 118 with a distal portion 120. Distal portion 120 of implantable medical lead 112 is positioned at a target site 114 within a heart 122 of a patient 116. Distal portion 120 may include one or more electrodes. Target site 114 may be located at a wall of a ventricle of heart 122. Lead 112 may be a bipolar or multipolar lead.

A clinician may maneuver distal portion 120 through the vasculature of patient 116 in order to position distal portion 120 at or near target site 114. For example, the clinician may guide distal portion 120 through the SVC to target site 114 on or in a ventricular wall of heart 122, e.g., at the apex of the right ventricle as illustrated in FIG. 1. In some examples, other pathways or techniques may be used to guide distal portions 120 into other target implant sites within the body of patient 116. Implantable medical device system 100 may include a delivery catheter and/or outer member (not shown), and implantable medical lead 112 may be guided and/or maneuvered within a lumen of the delivery catheter in order to approach target site 114.

Implantable medical lead 112 may include electrodes 124A and 124B (collectively, "electrodes 124") configured to be positioned on, within, or near cardiac tissue at or near target site 114. In some examples, electrodes 124 are configured to function as electrodes in order to, for example, provide pacing to heart 122. Electrodes 124 may be electrically connected to conductors (not shown) extending through lead body 118. In some examples, the conductors are electrically connected to therapy delivery circuitry of IMD 126, with the therapy delivery circuitry configured to provide electrical signals through the conductor to electrodes 124. Electrodes 124 may conduct the electrical signals to the target tissue of heart 122, causing the cardiac muscle, e.g., of the ventricles, to depolarize and, in turn, contract at a regular interval. Electrodes 124 may also be connected to sensing circuitry of IMD 126 via the conductors, and the sensing circuitry may sense activity of heart 122 via electrodes 124. Electrodes 124 may have various shapes such as tines, helices, screws, rings, and so on. Again, although a bipolar configuration of lead 112 including two electrodes 124 is illustrated in FIG. 1, in other examples IMD 126 may be coupled to leads including different numbers of electrodes, such as 1 electrode, three electrodes, or four electrodes.

In one or more examples, IMD 126 includes electronic circuitry contained within a polymeric enclosure where the circuitry may be configured to deliver cardiac pacing. In the example of FIG. 1, the electronic circuitry within IMD 126 may include therapy delivery circuitry electrically coupled to electrodes 124. The electronic circuitry within IMD 126 may also include sensing circuitry configured to sense electrical activity of heart 122 via electrodes 124. The therapy delivery circuitry may be configured to administer cardiac pacing via electrodes 124, e.g., by delivering pacing pulses in response to expiration of a timer and/or in response to detection of the activity (or absence thereof) of heart.

Figure 2:
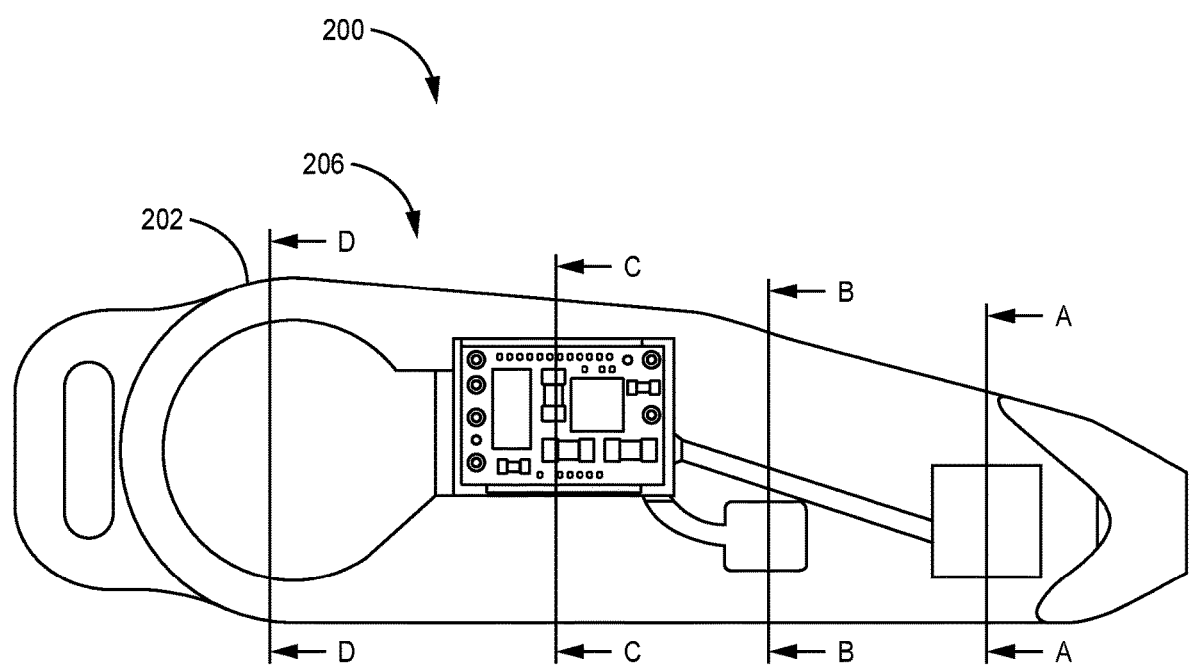
FIG. 2 is a top view of an implantable medical device in accordance with one or more aspects of this disclosure.

FIGS. 2 and 2A-2D illustrate an example of an implantable medical device (IMD) 200 having electronic circuitry 206 and a polymeric enclosure 202, where FIGS. 2A-2D show various cross-sections of the IMD 200 of FIG. 2. In one or more examples, the electronic circuitry, as described above, may include therapy delivery circuitry and/or sensing circuitry. In some examples, at least a portion of the polymeric enclosure 202, such as a single polymeric enclosure, is formed of epoxy. IMD 200 includes electronic circuitry contained within the polymeric enclosure 202. As described above, electronic circuitry may include sensing circuitry for receiving signals from electrodes and therapy delivery circuitry configured to deliver cardiac pacing. In some examples, electronic circuitry 206 includes processing circuitry for processing signals, and memory IMD 200 may also include a battery. In one or more examples, the IMD 200 is a small, temporary pacemaker with a single polymeric enclosure.

Figure 2A:
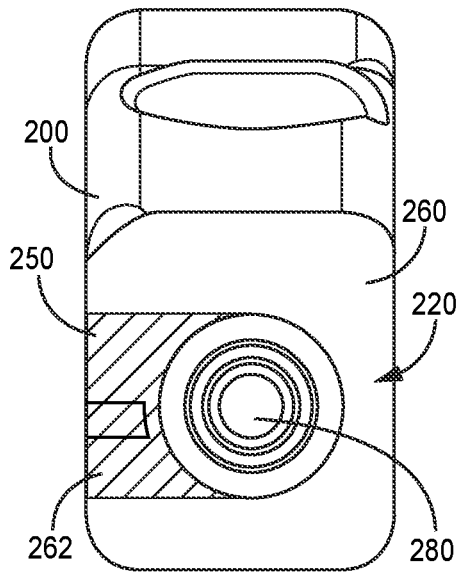
FIG. 2A is a cross-sectional view of the implantable device of FIG. 2, taken along 2A-2A in accordance with one or more aspects of this disclosure.
Figure 2B:
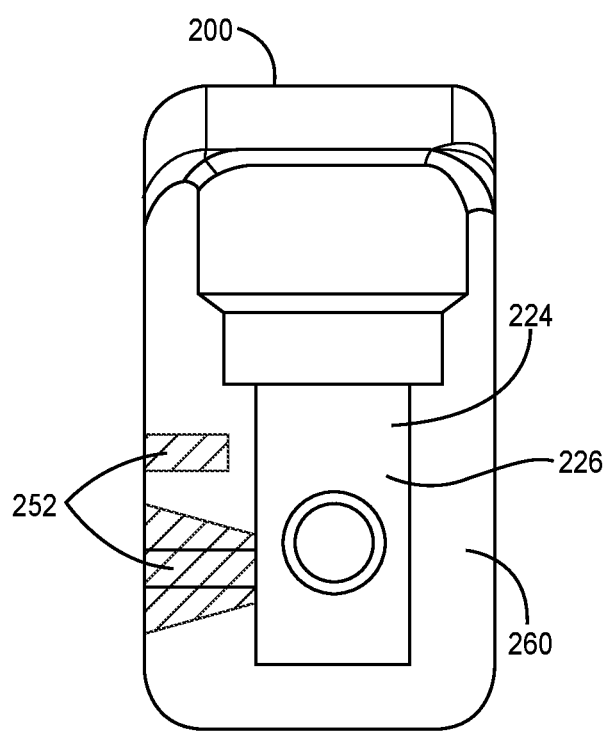
FIG. 2B is a cross-sectional view of the implantable device of FIG. 2, taken along 2B-2B of FIG. 2 in accordance with one or more aspects of this disclosure.
Figure 2C:
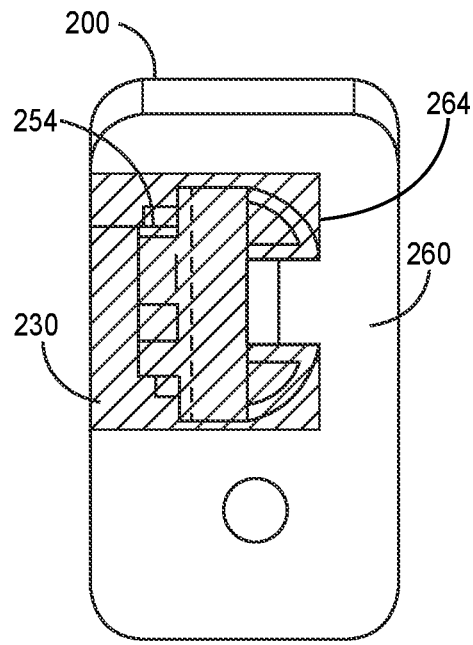
FIG. 2C is a cross-sectional view of the implantable device of FIG. 2, taken along 2C-2C of FIG. 2 in accordance with one or more aspects of this disclosure.

In one or more examples, implantable medical device 200 includes a preformed polymeric structure 260 having a first set of openings 262, where the first set of openings 262 may include one or more openings, as shown in FIGS. 2A and 2B. The first set of openings 262 are sized and configured to receive components therein. The preformed polymeric structure 260 may be 3D printed, molded, or cast from polymeric material.

In one or more examples, the implantable medical device 200 includes electrical and mechanical couplings 220 disposed within the first set of openings 262, as shown in FIG. 2A. The electrical and mechanical couplings 220 may be for an electrical contact for an implantable lead receptacle 280, which may include electrical and/or mechanical couplings. The implantable lead receptacle 280 allows for a lead to be mechanically inserted into the implantable medical device, and further allows for the lead to be mechanically and electrically coupled with the implantable medical device 200. In one or more examples, the electrical and mechanical couplings 220 include a multi beam connector.

Figure 5A:
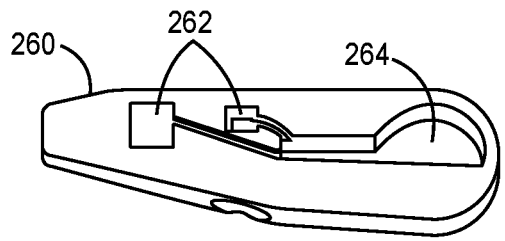
FIG. 5A illustrates a perspective top view of a preformed polymeric structure in accordance with one or more aspects of this disclosure.
Figure 5B:
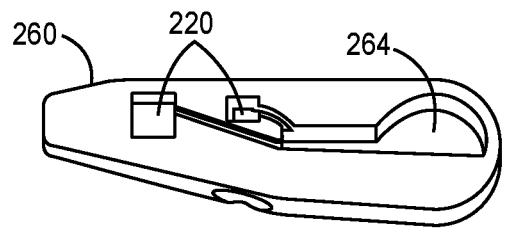
FIG. 5B illustrates a perspective top view of a preformed polymeric structure in accordance with one or more aspects of this disclosure.

In one or more examples, the implantable medical device 200 includes couplings 224 (FIG. 2B) disposed within the first set of openings 262 (FIG. 5B). The couplings 224 may be for an implantable lead receptacle 280, which may include electrical and/or mechanical couplings. The implantable lead receptacle 280 allows for a lead to be mechanically inserted into the implantable medical device, and further allows for the lead to be mechanically and electrically coupled with the implantable medical device 200. In one or more examples, the couplings 224 includes a set screw block 226. In one or more examples, the couplings include a setscrew block and setscrew.

Figure 2D:
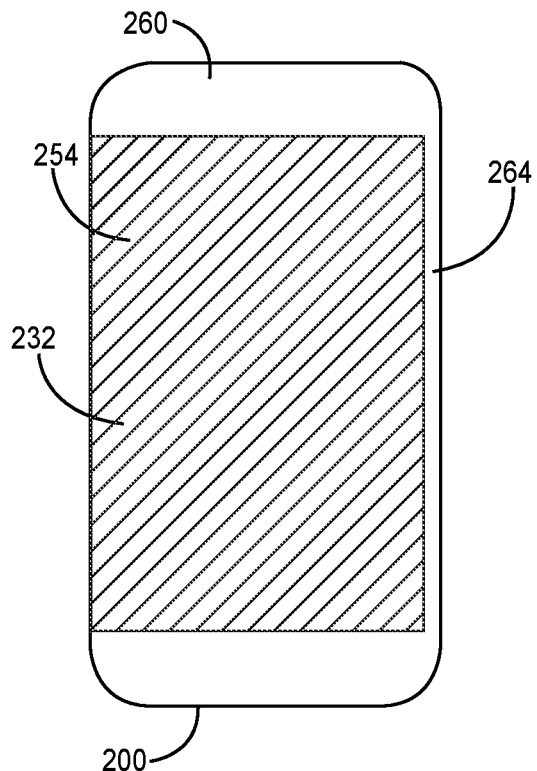
FIG. 2D is a cross-sectional view of the implantable device of FIG. 2, taken along 2D-2D of FIG. 2 in accordance with one or more aspects of this disclosure.
Figure 5C:
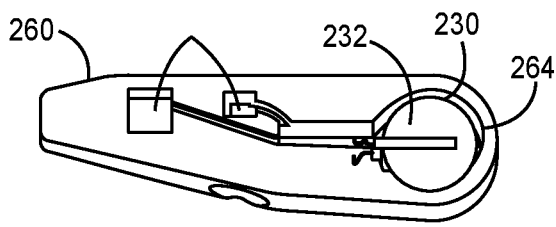
FIG. 5C illustrates a perspective top view of a preformed polymeric structure in accordance with one or more aspects of this disclosure.
Figure 5D:
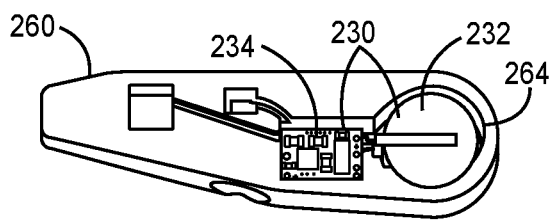
FIG. 5D illustrates a perspective top view of a preformed polymeric structure in accordance with one or more aspects of this disclosure.
Figure 5E:
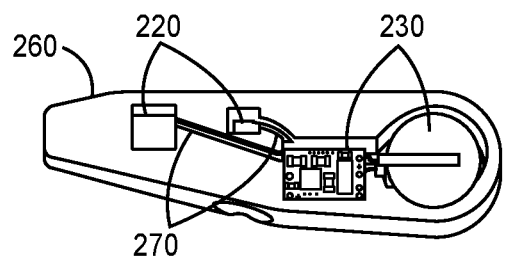
FIG. 5E illustrates a perspective top view of a preformed polymeric structure in accordance with one or more aspects of this disclosure.

In one or more examples, the preformed polymeric structure 260 of the implantable medical device 200 includes a second set of openings 264, where the second set of openings 264 may include one or more openings, as shown in FIGS. 5C and 5D. The second set of openings 264 are sized and configured to receive components therein. In one or more examples, the implantable medical device 200 includes a set of electronics 230 disposed within the second set of openings 264. In one example, the set of electronics 230 includes a hybrid board, as shown in FIG. 5C. The hybrid board may include various therapy sensing processing circuitry, as discussed above. In some examples, the set of electronics 230 includes a battery pack 232, as shown in FIG. 2D.

In one or more examples, the first set of openings 262 of the preformed polymeric structure 260 may be filled with a first material 250, for example backfilled around the components within the first set of openings 262. For example, polymeric material may be back filled with a first material around the first set of electronics 220 and couplings 224. The first material may be medical adhesive, such as medical grade silicone material. In one or more examples, the second set of openings 264 is filled with a second material 254. In some examples, the second material is epoxy. In one or more examples, the first material is different than the second material, and the first material is medical adhesive and the second material is epoxy. The first material and/or second material is filled around the couplings and electronic components of the implantable medical device 200. The first material and/or the second material, in combination with the preformed polymeric structure 260 which may provide a single polymeric enclosure for an implantable medical device 200, such as an implantable medical device 200 that is a small temporary pacemaker.

Figure 3:
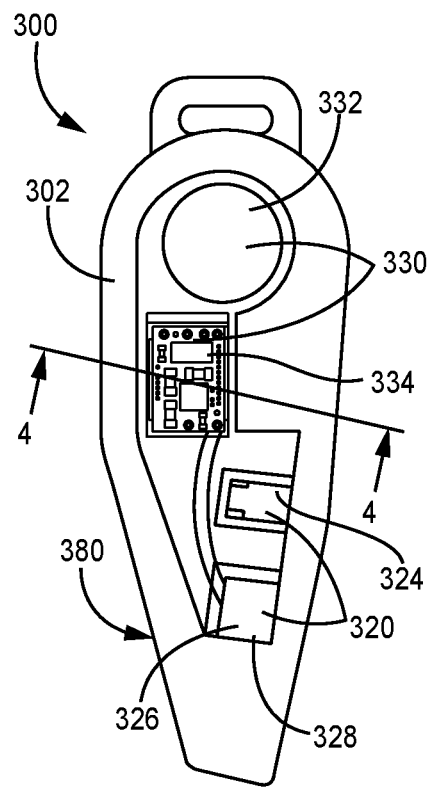
FIG. 3 is a top view of an implantable medical device in accordance with one or more aspects of this disclosure.
Figure 4:
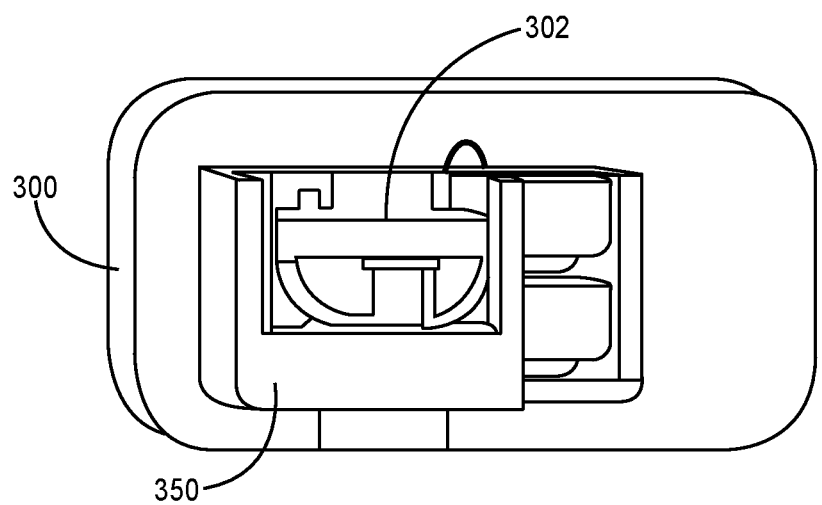
FIG. 4 is a cross-sectional view of the implantable device of FIG. 3, taken along 4-4 of FIG. 3 in accordance with one or more aspects of this disclosure.

FIGS. 3-4 illustrate an example of an implantable medical device 300 having a polymeric enclosure 302, where FIG. 4 shows a cross-section of the implantable medical device 300 of FIG. 3. The implantable medical device 300 may include sensing circuitry for receiving signals from electrodes. In one or more examples, the implantable medical device 300 includes electronic circuitry configured to deliver cardiac pacing contained within the polymeric enclosure 302. Sensing circuitry can include filtering circuitry and other circuitry for conditioning the sensed signals, as well as amplifiers and/or other circuitry configured to detect depolarizations or other features of the signals. Pacing circuitry may include capacitors switches, and or other circuitry for generating electrical pulses having amplitudes, widths, and timings. Processing circuitry may control pacing circuitry based on features detected by sensing circuity.

In some examples, the implantable medical device 300 includes processing circuitry for processing signals, memory, and a battery. In one or more examples, the implantable medical device 300 is a small, temporary pacemaker with a single polymeric enclosure.

In one or more examples, the implantable medical device 300 includes a set of electronics, such as electrical and mechanical couplings 320 where the electrical and mechanical couplings 320 may be for electrical contacts for an implantable lead receptacle 380, which may include electrical and/or mechanical couplings. The implantable lead receptacle 380 allows for a lead to be mechanically inserted into the implantable medical device, and further allows for the lead to be mechanically and electrically coupled with the implantable medical device 300. In one or more examples, the electrical and mechanical couplings 320 include a multi beam connector 328.

In one or more examples, the implantable medical device 300 include couplings 324 where the couplings 324 may be for an implantable lead receptacle 380, which may include electrical and/or mechanical couplings. The implantable lead receptacle 380 allows for a lead to be mechanically inserted into the implantable medical device, and further allows for the lead to be mechanically and electrically coupled with the implantable medical device 300. In one or more examples, the couplings 324 includes a set screw connector block 326. In one or more examples, the couplings include a setscrew block and setscrew.

In one or more examples, the implantable medical device 300 includes a set of electronics 330. In one example, the set of electronics 330 e.g., a hybrid board 334 that may include sensing circuitry, pacing circuitry, and processing circuitry. In some examples, the set of electronics 330 includes a battery pack 332.

In one or more examples, polymeric enclosure 302 may be formed of a polymeric material, such as first material 350. In one or more examples, the first material 350 may be molded around the components, including the electrical and mechanical couplings 220, and set of electronics 330, as shown in FIG. 4. The first material may be medical adhesive. In some examples, the first material is epoxy. The first material may provide a single polymeric enclosure for an implantable medical device 200, such as an implantable medical device 200 that is a small temporary pacemaker.

In one or more examples, a method for manufacturing an implantable medical device having a polymeric enclosure is disclosed herein. Referring to FIGS. 5A and 5B, the method includes providing a pre-formed polymeric structure 260, as shown in FIG. 5A. The pre-formed polymeric structure may be a molded structure or 3D printed of polymeric material, for example. The method further includes inserting electrical and mechanical couplings 220 into a first set of openings 262 within the pre-formed polymeric structure 260, as shown in FIG. 5B. In one or more examples, the electrical and mechanical couplings include a multi beam connector (MBC). In one or more examples, the couplings include electrical and/or mechanical couplings. In one or more examples, the couplings include a set screw connector block. Referring to FIGS. 5C and 5D, a set of electronics 230 may be disposed within a second set of openings 264. The set of electronics 230 may include a battery pack 232 and/or a hybrid board 234. Electrical connections 270 are disposed within the polymeric structure 260 between the electrical and mechanical couplings 220 and the set of electronics 230, and are electrically connected to each of the electrical and mechanical couplings 220 and the set of electronics, for example by solder, so that the electrical and mechanical couplings 220 are electrically coupled with the set of electronics 230.

Figure 5F:
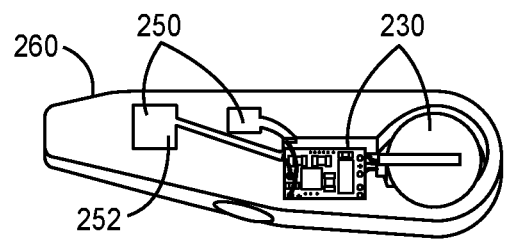
FIG. 5F illustrates a perspective top view of a preformed polymeric structure in accordance with one or more aspects of this disclosure.
Figure 5G:
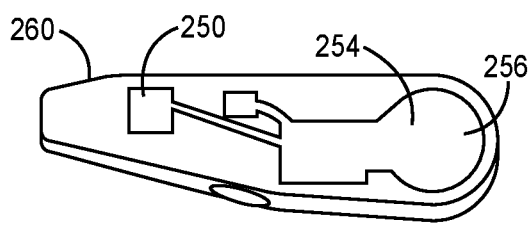
FIG. 5G illustrates a perspective top view of a preformed polymeric structure in accordance with one or more aspects of this disclosure.

The method further may include disposing a setscrew access grommet within the polymeric structure 260, and filling the first set of openings 262 around the electrical and mechanical couplings 220 with a first polymeric material 250, as shown in FIG. 5F. In one or more examples, the first polymeric material includes medical adhesive 252. In some examples, the medical adhesive may be medical grade silicone. In one or more examples, the medical adhesive may be room temperature vulcanization silicone (RTV). As shown in FIG. 5G, the second set of openings 264 may be filled with a second polymeric material 254, where the filling of the second set of openings is disposed around the set of electronics 230. In one or more examples, the first polymeric material 250 is different than the second polymeric material 254. In one or more examples, the first polymeric material 250 is medical adhesive and the second polymeric material 254 is epoxy 256.

Figure 6:
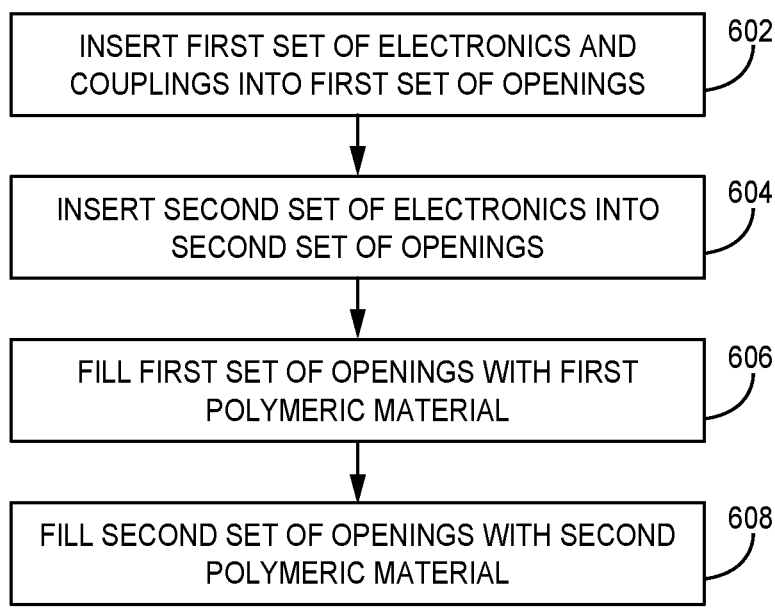
FIG. 6 is a flowchart illustrating an example method for forming an implantable medical device in accordance with one or more aspects of this disclosure.

In one or more examples, a method includes inserting an electrical and mechanical couplings for an implantable lead receptacle into a first set of openings (602), as shown in FIG. 6. In one or more examples, the couplings may include mechanical couplings and/or electrical couplings. In some examples, inserting the electrical and mechanical couplings includes inserting a set screw block, and a set screw, and/or a multi beam connector. In one or more examples, a method includes inserting a set of electronics into a second set of openings (604). In some examples, inserting the electrical and mechanical couplings includes inserting battery components and/or a hybrid antenna assembly. The method may further include electrically coupling the electrical and mechanical couplings with the set of electronics. In some examples, electrically coupling may include welding and/or soldering processes. The method further may include filling the first set of openings with a first polymeric material and disposing the first polymeric material around the electronics and couplings (606). The method may further include filling the second set of openings with a second polymeric material (608) to form a polymeric enclosure for the implantable medical device with polymeric material, where the polymeric material may be epoxy and/or medical adhesive.

Figure 7A:
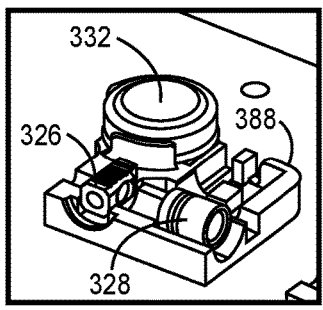
FIG. 7A illustrates a portion of an implantable medical device during formation of the implantable medical device in accordance with one or more aspects of this disclosure.
Figure 7B:
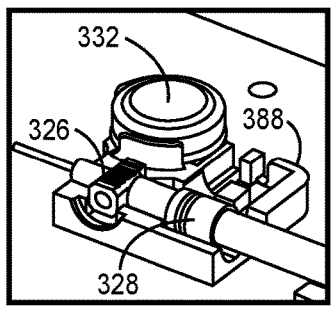
FIG. 7B illustrates a portion of an implantable medical device during formation of the implantable medical device in accordance with one or more aspects of this disclosure.
Figure 7C:
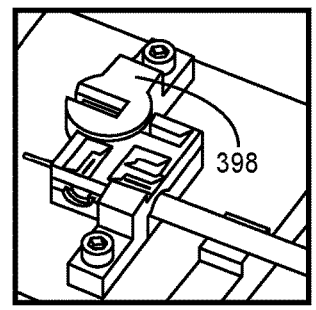
FIG. 7C illustrates a portion of an implantable medical device during formation of the implantable medical device in accordance with one or more aspects of this disclosure.
Figure 7D:
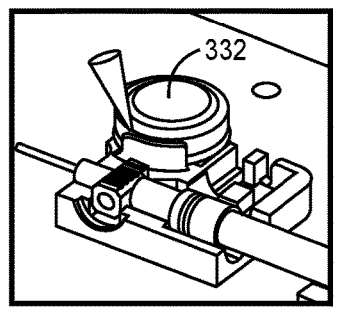
FIG. 7D illustrates a portion of an implantable medical device during formation of the implantable medical device in accordance with one or more aspects of this disclosure.
Figure 7E:
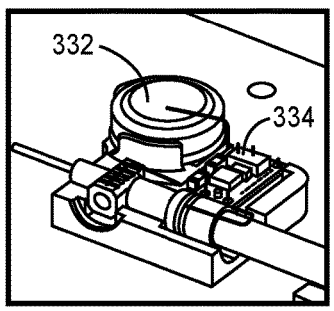
FIG. 7E illustrates a portion of an implantable medical device during formation of the implantable medical device in accordance with one or more aspects of this disclosure.
Figure 7F:
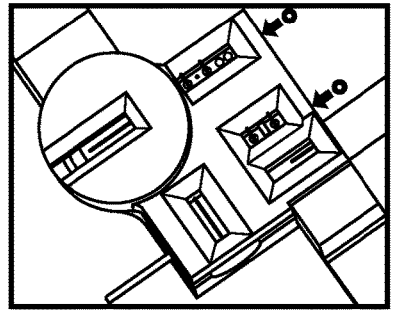
FIG. 7F illustrates a portion of an implantable medical device during formation of the implantable medical device in accordance with one or more aspects of this disclosure.
Figure 7G:
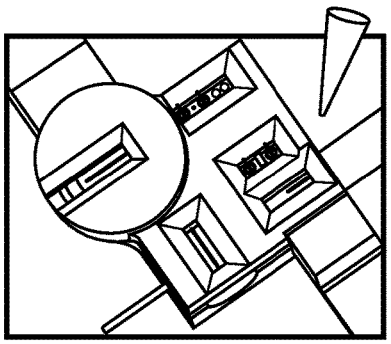
FIG. 7G illustrates a portion of an implantable medical device during formation of the implantable medical device in accordance with one or more aspects of this disclosure.
Figure 7H:
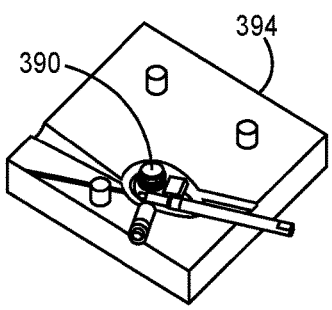
FIG. 7H illustrates a portion of an implantable medical device during formation of the implantable medical device in accordance with one or more aspects of this disclosure.
Figure 7I:
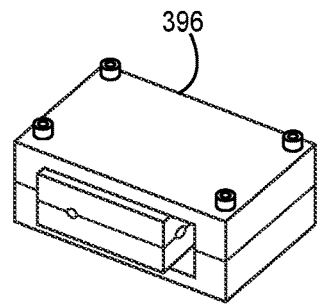
FIG. 7I illustrates a portion of an implantable medical device during formation of the implantable medical device in accordance with one or more aspects of this disclosure.
Figure 7J:
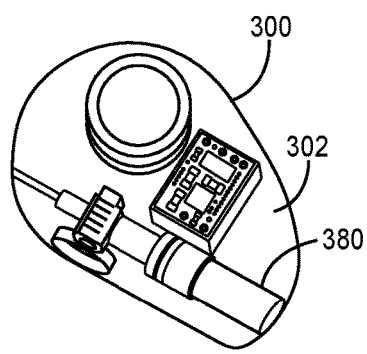
FIG. 7J illustrates a formed implantable medical device in accordance with one or more aspects of this disclosure.

In one or more examples, a method for manufacturing an implantable medical device having a polymeric enclosure is disclosed herein. In some examples, the polymeric enclosure is molded around components of the implantable medical device. Referring to FIG. 7A, a set of electronics and electrical and mechanical couplings may be disposed within a fixture 388. In some examples, the electrical and mechanical couplings may include a set screw block 326, multi beam connector 328, and the set of electronics may include battery pack 332 (FIG. 7A) and hybrid-antenna assembly 334 (FIG. 7E). Hybrid-antenna assembly may further include sensing, therapy, or processing circuitries. In one or more examples, hybrid-antenna assembly may include communication circuitry, for example for wireless communication with external devices. An electrical connection and/or a clamping device may be disposed amongst the set of electronics in preparation for electrically connecting the components. In some examples, a Teflon-coated pin is routed through the set screw block 326 and the multi beam connector 328, as shown in FIG. 7B. In one or more embodiments, niobium pins are added, and a retention device 398 for the resistance weld step is added (FIG. 7D). The electronics may be electrically coupled with each other. For example, FIGS. 7F and 7G illustrate placing solder preforms on the hybrid-antenna assembly 334, and the solder is reflowed, for example using a laser, to electrically couple the hybrid antenna assembly 334, battery pack 332, multi beam connector 328 and the set screw block 326, and forming a subassembly 390. The subassembly 390 may be disposed in a half-mold 394, as shown in FIG. 7H. In one or more examples, the full mold 396 is formed by placing the other portion on the half-mold 394 and closing the mold. Polymeric material, such as, but not limited to, epoxy, is disposed within the mold 394, and filled around the components of the subassembly 390. The polymeric material is cured, for example by heat. In some examples, the mold is placed in an oven at 55 degrees C. for two hours allowing the polymeric to cure. As shown in FIG. 7J, an implantable medical device 300 having a polymeric enclosure 302 with a lead receptacle 380 is formed.

Figure 8:
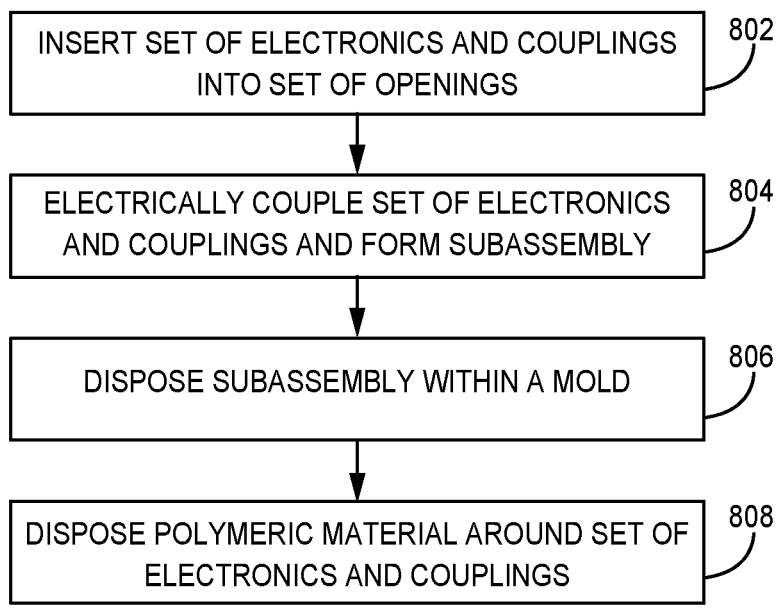
FIG. 8 is a flowchart illustrating an example method for forming an implantable medical device in accordance with one or more aspects of this disclosure.

In one or more examples, a method includes inserting a set of electronics and couplings for an implantable lead receptacle into a set of openings (802), as shown in FIG. 8. In some examples, inserting the set of electronics and couplings includes inserting battery components, an antenna assembly, a set screw block, and a set screw. In one or more examples, the couplings may include mechanical couplings and/or electrical couplings. The method may further include electrically coupling the set of electronics with the couplings and forming a subassembly (804). The subassembly may further be disposed in a mold (806), and polymeric material disposed around the electronics and couplings (808) to form a polymeric enclosure for the implantable medical device with polymeric material, where the polymeric material may be epoxy and/or medical adhesive.

The following numbered examples may illustrate one or more aspects of this disclosure:

Example 1. A method for forming an implantable medical device with a polymeric enclosure, the method comprising: inserting electrical and mechanical couplings for an implantable medical lead receptacle into a first set of openings of a pre-formed polymeric structure; inserting a set of electronics within a second set of openings of the pre-formed polymeric structure; filling the first set of openings around the electrical and mechanical couplings with a first polymeric material; and filling the second set of openings around the set of electronics with a second polymeric material.

Example 2. The method of example 1, wherein the first polymeric material is different than the second polymeric material.

Example 3. The method of example 1 or 2, wherein inserting the set of electronics includes inserting battery components and an antenna assembly into the second set of openings.

Example 4. The method of any of examples 1 to 3, wherein inserting the electrical and mechanical couplings and mechanical couplings into a first set of openings includes inserting a set screw within the first set of openings.

Example 5. The method of any of examples 1 to 4, further comprising electrically coupling the electrical and mechanical couplings with the set of electronics.

Example 6. The method of any of examples 1 to 5, further comprising 3D-printing the pre-formed structure.

Example 7. The method of any of examples 1 to 6, wherein filling the first set of openings and filling the second set of openings comprises injection molding.

Example 8. The method of any of examples 1 to 7, wherein the first polymeric material comprises medical adhesive.

Example 9. The method of any of examples 1 to 8, wherein the second polymeric material comprises epoxy.

Example 10. A method for forming an implantable medical device with a polymeric enclosure, the method comprising: inserting a set of electronics and mechanical couplings into a set of openings of a fixture; electrically coupling the set of electronics and couplings creating a subassembly; disposing the subassembly within a mold; and disposing polymeric material around the set of electronics and mechanical couplings within the mold forming the polymeric enclosure for the implantable medical device with the polymeric material.

Example 11. The method of example 10, wherein the polymeric material is epoxy.

Example 12. The method of example 10 or 11, wherein inserting the set of electronics and mechanical couplings includes inserting battery components, an antenna assembly, a set screw block, and a set screw.

Example 13. An implantable medical device comprising: electronic circuitry configured to deliver cardiac pacing; couplings for an implantable medical lead receptacle, at least some of the couplings electrically connected with the electronic circuitry; and a polymeric enclosure having the electronic circuitry contained therein, the polymeric enclosure formed of polymeric material filled around the electronic circuitry and couplings and forming the implantable medical lead receptacle.

Example 14. The implantable medical device as recited in example 13, wherein the implantable medical device includes a first set of openings filled with a first material and a second set of openings filled with a second material, and the first material is different than the second material.

Example 15. The implantable medical device of example 14, wherein the first material is medical adhesive.

Example 16. The implantable medical device of example 14 or 15, wherein the second material is epoxy.

Example 17. The implantable medical device of any of examples 13 to 16, wherein the polymeric enclosure is formed of epoxy.

Example 18. The implantable medical device of any of examples 13 to 17, wherein the couplings include a setscrew block and setscrew.

Various aspects of the techniques may be implemented within one or more processing circuitries, including one or more microprocessors, DSPs, ASICs, FPGAs, or any other equivalent integrated or discrete logic circuitry, as well as any combinations of such components, embodied in external devices, such as physician or patient external devices, electrical stimulators, or other devices. The term "processing circuitry" may generally refer to any of the foregoing logic circuitry, alone or in combination with other logic circuitry or any other equivalent circuitry.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media may include computer-readable storage media forming a tangible, non-transitory medium. Instructions may be executed by one or more processing circuitries, such as one or more DSPs, ASICs, FPGAs, general purpose microprocessors, or other equivalent integrated or discrete logic circuitry. Accordingly, the term "processing circuitry," as used herein may refer to one or more of any of the foregoing structure or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external device, a combination of an IMD and external device, an integrated circuit (IC) or a set of ICs, and/or discrete electrical circuitry, residing in an IMD and/or external device.

The invention claimed is:

1. An implantable medical device comprising:
   electronic circuitry including a battery pack and a hybrid board configured to generate and deliver cardiac pacing;
   couplings for an implantable medical lead receptacle, at least some of the couplings electrically connected with the electronic circuitry; and
   a polymeric enclosure having the electronic circuitry contained therein, the polymeric enclosure formed of at least one polymeric material filled around the electronic circuitry and couplings and also forming the implantable medical lead receptacle, wherein the at least one polymeric material includes a first material and a second material, wherein the implantable medical device includes a first set of openings containing the couplings for the implantable medical lead and filled with the first material and a second set of openings containing the electronic circuitry and filled with the second material, and wherein the first material is different than the second material.

2. The implantable medical device of claim 1, wherein the first material is medical adhesive.

3. The implantable medical device of claim 1, wherein the second material is epoxy.

4. The implantable medical device of claim 1, wherein the first material is medical adhesive, and the second material is epoxy.

5. The implantable medical device of claim 1, wherein the couplings include a setscrew block and a setscrew.

* * * * *